US00PP11453P

United States Patent [19]

Treiber et al.

[11] Patent Number: Plant 11,453

[45] Date of Patent: Jul. 18, 2000

[54] NANDINA PLANT NAMED 'COLERNO'

[75] Inventors: Tom Treiber, San Antonio; James Spivey, Devine, both of Tex.

[73] Assignee: Color Spot Nurseries, Inc., Pleasant Hill, Calif.

[21] Appl. No.: 09/165,028

[22] Filed: Oct. 2, 1998

[51] Int. Cl.[7] ..... A01H 5/00

[52] U.S. Cl. ..... Plt./235

[58] Field of Search ..... Plt./235

*Primary Examiner*—Howard J. Locker
*Assistant Examiner*—Wendy A Baker
*Attorney, Agent, or Firm*—C. A. Whealy

[57] ABSTRACT

A new and distinct cultivar of Nandina plant named 'Colerno', characterized by its upright, compact and dense plant habit; low vigor, slow growth rate; and unique dark red purple-colored young foliage and dark green-colored mature foliage. Dark red purple color of young foliage is retained year-round.

1 Drawing Sheet

BACKGROUND OF THE INVENTION

The present invention relates to a new and distinct cultivar of Nandina, botanically known as *Nandina domestica,* and hereinafter referred to by the cultivar name Colerno.

The new Nandina is a product of a planned breeding program conducted by the Inventors in San Antonio, Tex. The objective of the breeding program was to create new Nandinas with unique leaf color. The new Nandina originated from a self-pollination of plants of an unnamed selection of *Nandina domestica.*

The cultivar Colerno was discovered and selected by the Inventors as a single plant within a population of progeny plants in a controlled environment in San Antonio, Tex. in June, 1991. The selection of this plant was based on its unique and long-lasting dark red purple-colored young foliage in contrast to the typical green-colored young foliage of the other progeny plants.

Asexual reproduction of the new Nandina by terminal cuttings taken in a controlled environment in San Antonio, Tex. has shown that the unique features of this new Nandina are stable and reproduced true to type in successive generations.

BRIEF SUMMARY OF THE INVENTION

Plants of the new Nandina have not been observed under all possible environmental conditions. The phenotype may vary somewhat with variations in environment such as temperature, daylength, light intensity, nutrition and water status without, however, any variance in genotype.

The following traits have been repeatedly observed and are determined to be the unique characteristics of 'Colerno'. These characteristics in combination distinguish 'Colerno' as a new and distinct cultivar:

1. Upright, compact and dense plant habit.
2. Low vigor, slow growth rate.
3. Unique dark red purple-colored young foliage and dark green-colored mature foliage. Dark red purple color of young foliage is retained year-round.

BRIEF DESCRIPTION OF THE PHOTOGRAPH

The accompanying colored photograph illustrates the overall appearance of the new Nandina, showing the colors as true as it is reasonably possible to obtain in colored reproductions of this type. The photograph comprises a top perspective view of a typical containerized plant of 'Colerno'. Foliage colors in the photograph may appear different from the actual colors due to light reflectance.

DETAILED BOTANICAL DESCRIPTION

The following observations, measurements, values, and comparisons describe plants grown in San Antonio and Keller, Tex., under outdoor conditions which closely approximate commercial production conditions. Plants used for the description were grown in 12.5-cm containers and were approximately 10 months old.

In the following description, color references are made to The Royal Horticultural Society Colour Chart except where general terms of ordinary dictionary significance are used.

Botanical classification: *Nandina domestica* cultivar Colerno.

Parentage: Self-pollination of an unnamed selection of *Nandina domestica.*

Propagation:

- *Type.*—By terminal cuttings.
- *Time to initiate roots.*—Sunmmer: About 21 to 28 days at temperatures of 29 to 35° C. Winter: About 28 to 42 days at temperatures of 18 to 24° C.
- *Time to develop roots.*—Summer: About 70 to 100 days at temperatures of 29 to 35° C. Winter: About 100 to 130 days at temperatures of 18 to 24° C.
- *Rooting habit.*—Numerous, fibrous.

Plant description:

- *Plant form and growth habit.*—Perennial evergreen shrub, upright, mostly rounded, leaves horizontal to somewhat weeping, compact and dense plant habit.
- *Vigor.*—Low; slow growth rate.
- *Plant size.*—About 31 cm in height and about 51 cm in width. Plants about 18 months old typically attain a height of about 76 cm and a width of about 61 to 76 cm.
- *Stem description.*—Diameter: About 5 mm. Internode length: About 2 cm. Color: Closest to 187B to 187A. Texture: Smooth longitudinally ridged.

Foliage description:

- *Arrangement.*—Compound, typically 3-pinnate.
- *Leaf length.*—About 31 cm.
- *Leaf width.*—About 21 cm.
- *Leaflet length.*—About 5.1 cm.
- *Leaflet width.*—About 1.1 cm.
- *Leaflet shape.*—Lanceolate.
- *Leaflet apex.*—Sharply acute.

*Leaflet base.*—Attenuate.

*Leaflet margin.*—Entire.

*Leaflet texture.*—Upper surface: Smooth. Lower surface: Midvein pubescent and prominent.

*Leaflet aspect.*—Flat or reflexed.

*Leaflet color.*—Young leaflets, upper surface: Very dark red purple, close to 187A. Dark red purple color is retained year-round. Young leaflets, lower surface: Dulled, 183B. Intermediate leaflets, upper surface: Dark green with red purple hues. Intermediate leaflets, lower surface: Medium green with reddish hues. Mature leaflets, upper surface: Dark green, darker than 147A, close to 139A. Mature leaflets, lower surface: Close to 147B.

*Rachis.*—Length: About 31 cm. Diameter: About 2 mm. Color: Young leaflets: Close to 187A. Mature leaflets: Darker than 147A, close to 139A. Texture: Flexible, longitudinally ridged.

Flower description: Flowers typical of species.

*Natural flowering season.*—Spring.

*Flower arrangement.*—Numerous single perfect flowers arranged in terminal panicles.

*Flower size.*—Small, about 7 mm by 3 mm.

*Flower/flower bud color.*—White with reddish overtones.

Disease resistance: Resistance to diseases common to plants of Nandina has not been observed.

Seed production: To date, production of berries has not been observed.

It is claimed:

1. A new and distinct Nandina plant named 'Colerno', as illustrated and described.

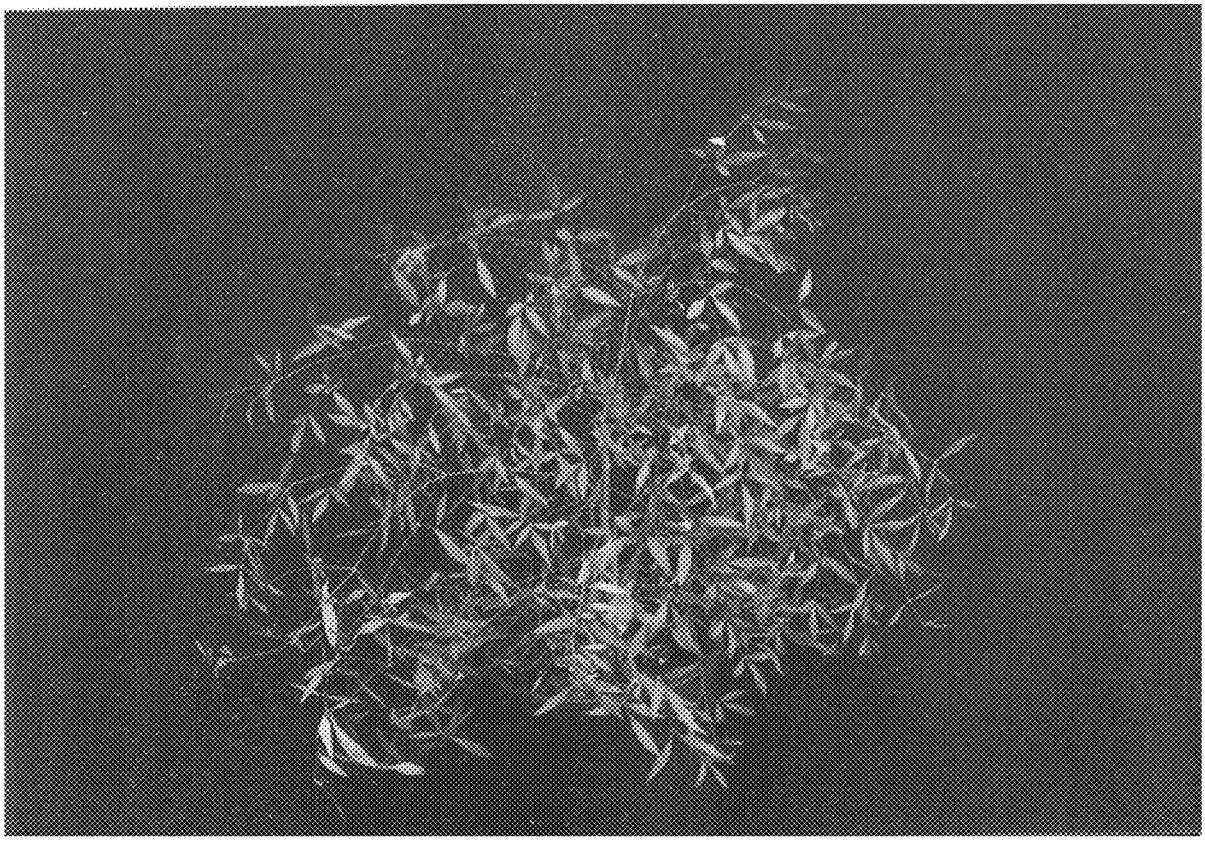

* * * * *